(12) United States Patent
Stout

(10) Patent No.: US 9,307,898 B2
(45) Date of Patent: Apr. 12, 2016

(54) MULTI-FUNCTION HEALTH PROFESSIONAL TOOL

(71) Applicant: Frank Stout, Webster Groves, MO (US)

(72) Inventor: Frank Stout, Webster Groves, MO (US)

( * ) Notice: Subject to any disclaimer, the term of this patent is extended or adjusted under 35 U.S.C. 154(b) by 0 days.

(21) Appl. No.: 14/292,177

(22) Filed: May 30, 2014

(65) Prior Publication Data

US 2014/0352075 A1 Dec. 4, 2014

Related U.S. Application Data

(60) Provisional application No. 61/829,095, filed on May 30, 2013.

(51) Int. Cl.
| | |
|---|---|
| *B26B 11/00* | (2006.01) |
| *A61B 3/00* | (2006.01) |
| *A61B 9/00* | (2006.01) |
| *A61B 5/107* | (2006.01) |
| *A61F 15/02* | (2006.01) |
| *A61B 5/0402* | (2006.01) |

(52) U.S. Cl.
CPC .............. *A61B 3/0008* (2013.01); *A61B 5/1072* (2013.01); *A61B 9/00* (2013.01); *A61B 5/04023* (2013.01); *A61B 2560/0425* (2013.01); *A61F 15/02* (2013.01)

(58) Field of Classification Search
CPC ........... B26B 11/00; B26B 13/22; B25F 1/00; A61B 2560/0425; A61B 9/00; A61B 5/1072; A61B 5/04023; A61B 3/0008; A61F 15/02

USPC ........................................ 7/163, 164, 131, 135
See application file for complete search history.

(56) References Cited

U.S. PATENT DOCUMENTS

| | | | | |
|---|---|---|---|---|
| 389,553 | A * | 9/1888 | Diefendorf | 7/131 |
| 553,579 | A * | 1/1896 | Frye | B25B 7/22 30/131 |
| D57,097 | S * | 2/1921 | Zylka | D8/55 |
| 4,037,276 | A * | 7/1977 | Brinker | 7/135 |
| 4,485,507 | A * | 12/1984 | Kantwerk | 7/135 |
| 5,280,659 | A * | 1/1994 | Park | B25F 1/003 7/107 |
| 6,647,842 | B1 * | 11/2003 | Krasik-Geiger et al. | 83/13 |
| 2009/0106984 | A1 * | 4/2009 | Braswell | 30/254 |
| 2011/0138631 | A1 * | 6/2011 | Smith | B26B 13/08 30/146 |
| 2012/0195027 | A1 * | 8/2012 | Russ et al. | 362/119 |
| 2013/0046323 | A1 * | 2/2013 | Whitaker | 606/174 |

* cited by examiner

*Primary Examiner* — Hadi Shakeri
*Assistant Examiner* — Danny Hong
(74) *Attorney, Agent, or Firm* — Polster, Lieder, Woodruff & Lucchesi, L.C.

(57) ABSTRACT

A multifunction health professional tool, having a pair of scissors with a pair of blades and a pair of handles connected by a pair of shanks. The tool also includes a Babinski reflex hammer detachably connected to one of the handles, a Taylor reflex hammer having a first portion connected to one of the handles and a second portion connected to the opposing handle, a slide ruler attached to one of the shanks, and a pupil dilator light attached to one of the shanks.

16 Claims, 18 Drawing Sheets

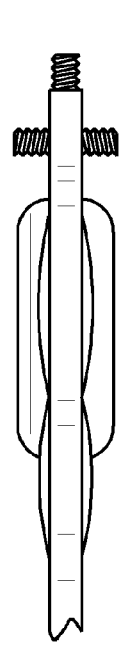 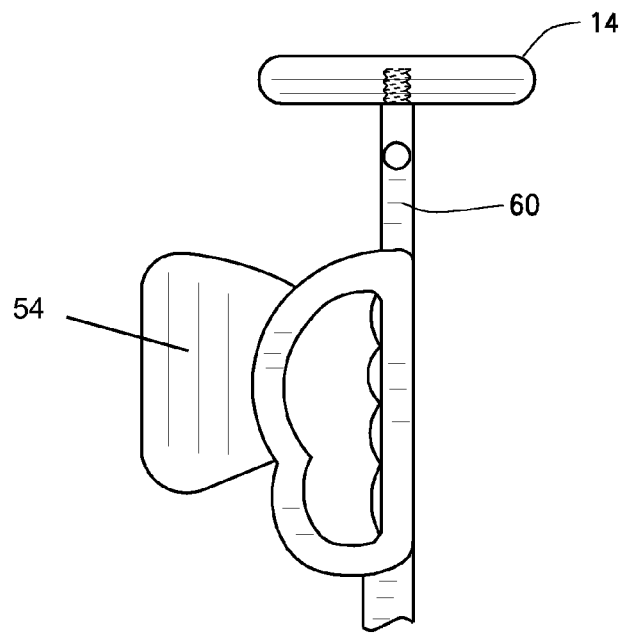
FIG. 3A  FIG. 3B
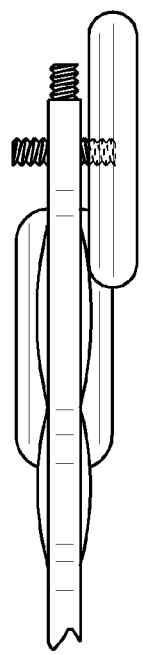 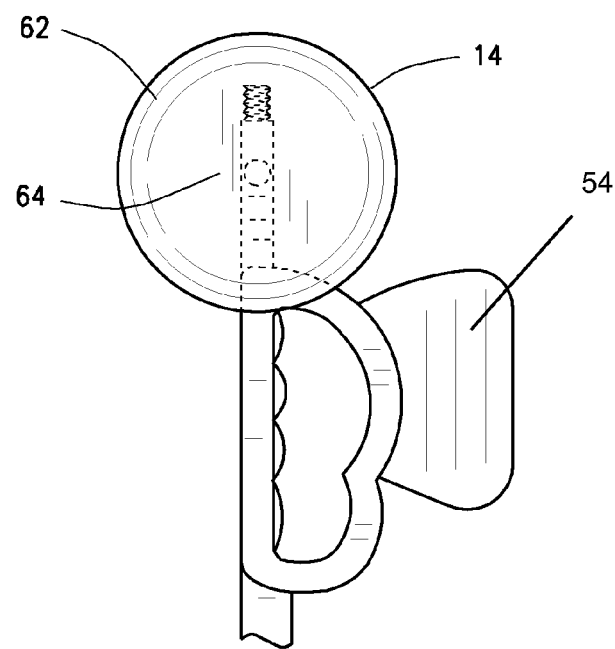
FIG. 3C  FIG. 3D

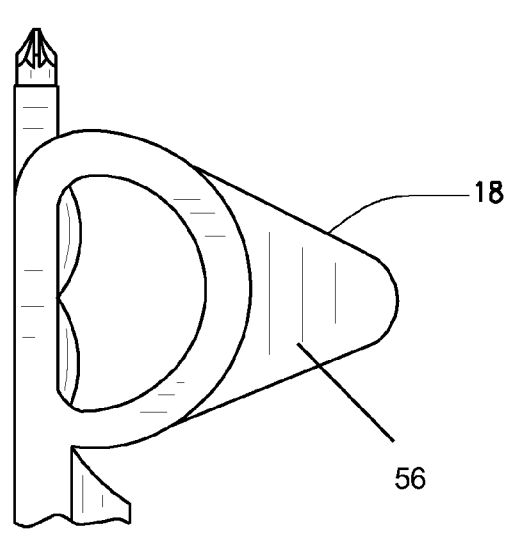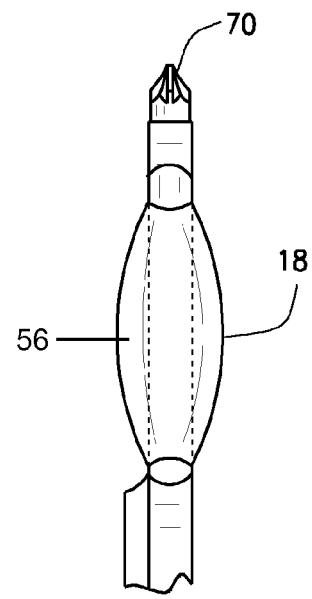
FIG. 4A          FIG. 4B
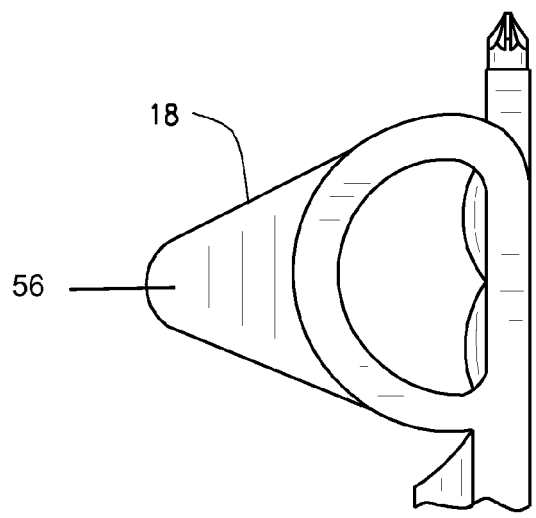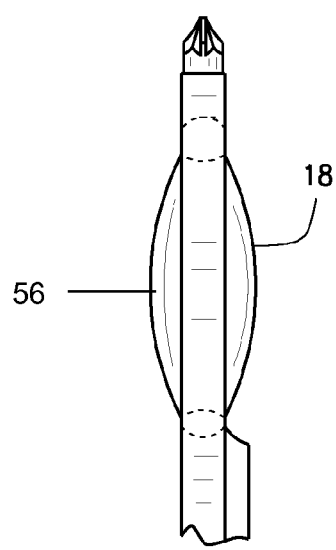
FIG. 4C          FIG. 4D

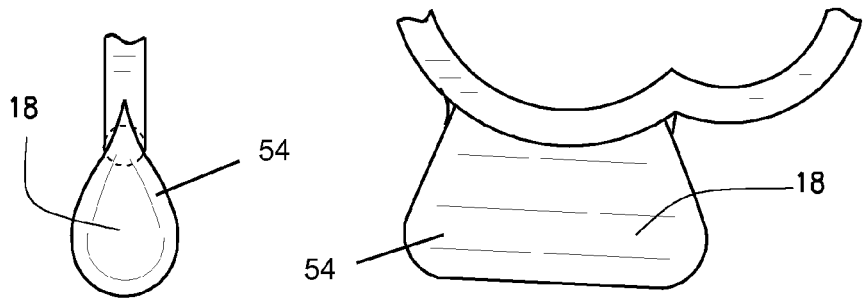
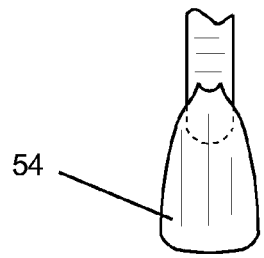
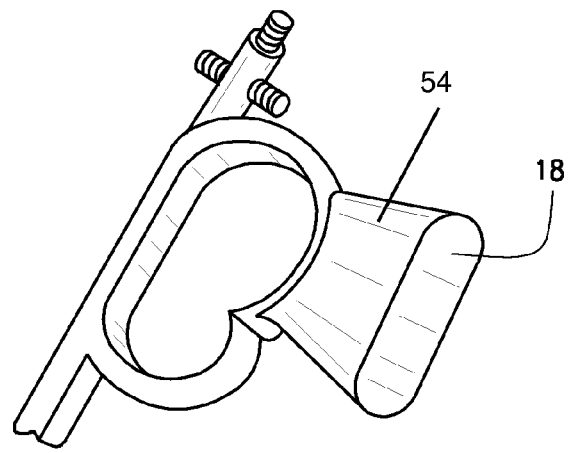
FIG.4E   FIG.5A
FIG.5B   FIG.5C
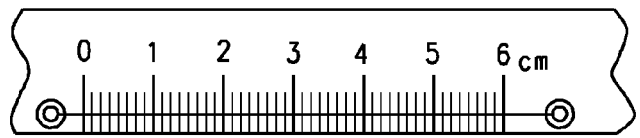
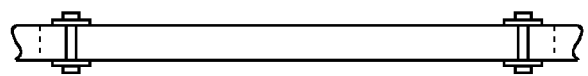
FIG.6A
FIG.6B

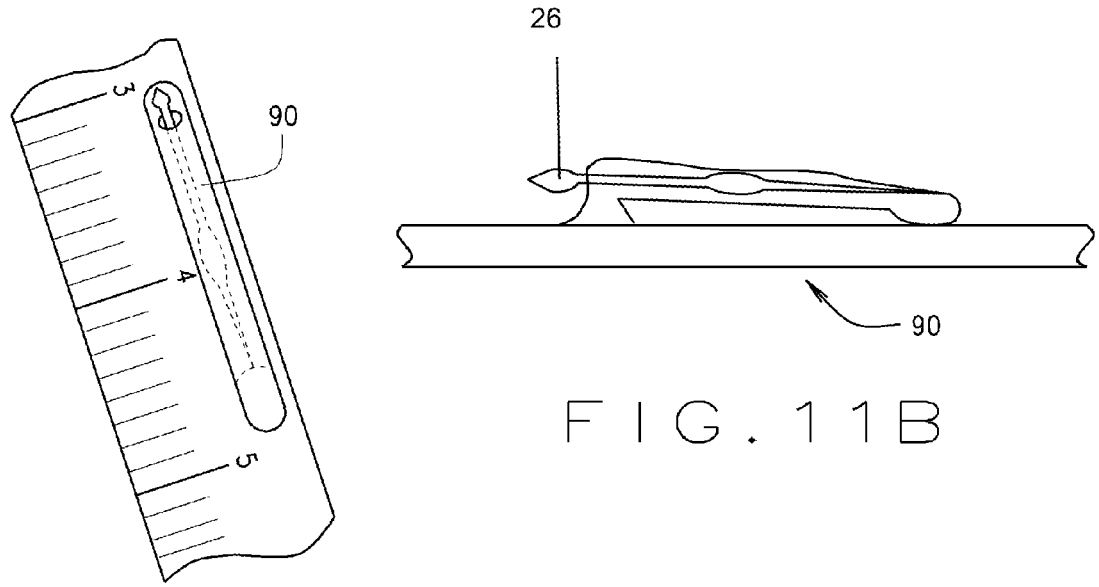
FIG. 11B
FIG. 11A
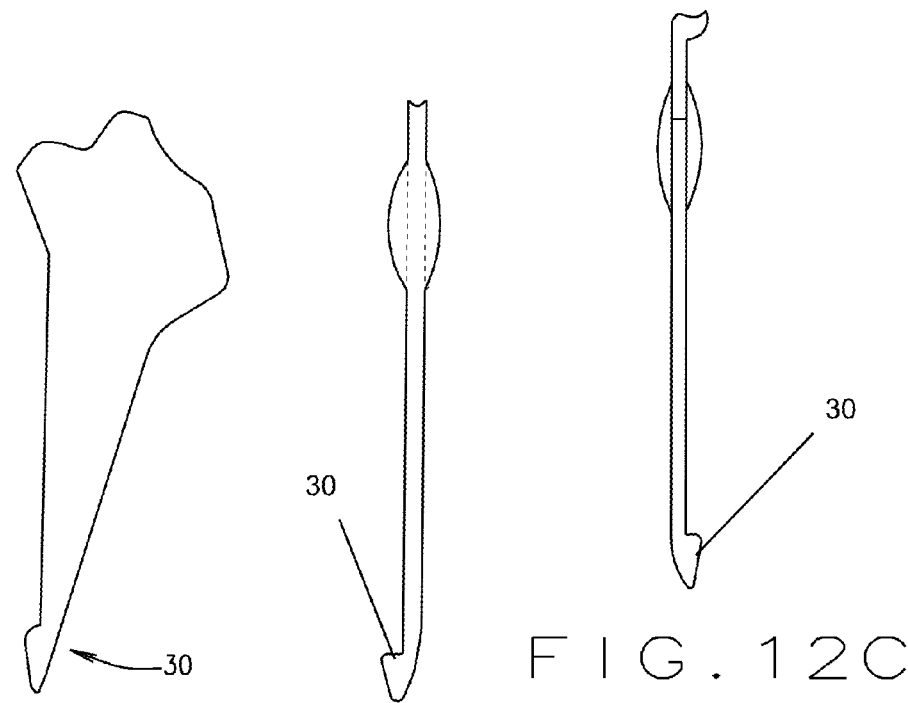
FIG. 12C
FIG. 12A  FIG. 12B

MULTI-FUNCTION HEALTH PROFESSIONAL TOOL

CROSS-REFERENCE TO RELATED APPLICATIONS

This Non-Provisional application claims priority to U.S. Provisional Application Ser. No. 61/829,095 filed May 30, 2013, and which is incorporated herein by reference.

STATEMENT REGARDING FEDERALLY SPONSORED RESEARCH

Not Applicable.

BACKGROUND

The invention relates to a tool for healthcare professionals, and more particularly to a multi-function tool for healthcare professionals.

The medical profession relies on a variety of different tools to diagnosis and treat patients. Many of these tools are used on a daily basis. However, the large number of tools make it impractical for a medical professional to keep all these tools on their person at all times.

Therefore, what is needed is a multi-function tool that incorporates many of the common medical professional tools.

DESCRIPTION OF THE DRAWINGS

In the accompanying drawings which form part of the specification:

FIG. 3A is an enlarged left side view of an integrated Babinski reflex hammer of the multi-function tool;

FIG. 3B is an enlarged front view of the integrated Babinski reflex hammer portion of the multi-function tool;

FIG. 3C is an enlarged right side view of the integrated Babinski reflex hammer of the multi-function tool;

FIG. 3D is an enlarged rear view of the integrated Babinski reflex hammer of the multi-function tool;

FIG. 4A is an enlarged front view of an integrated first portion of a Taylor reflex hammer of the multi-function tool;

FIG. 4B is an enlarged left side view of the integrated first portion of the Taylor reflex hammer of the multi-function tool;

FIG. 4C is an enlarged rear view of the integrated first portion of the Taylor reflex hammer of the multi-function tool;

FIG. 4D is an enlarged right side view of the integrated first portion of the Taylor reflex hammer of the multi-function tool;

FIG. 4E is an enlarged cross-section view of the integrated first portion of the Taylor reflex hammer of the multi-function tool'

FIG. 5A is an enlarged front view of an integrated second portion of a Taylor reflex hammer of the multi-function tool;

FIG. 5B is an enlarged cross-section view of the integrated second portion of the Taylor reflex hammer of the multi-function tool;

FIG. 5C is an enlarged perspective view of the integrated second portion of the Taylor reflex hammer of the multi-function tool;

FIG. 6A is an enlarged front view of an integrated slide ruler of the multi-function tool;

FIG. 6B is an enlarged side view of the integrated slide ruler of the multi-function tool;

FIG. 11A is an enlarged front view of an integrated pocket clasp of the multi-function tool;

FIG. 11B is an enlarged side view of the integrated pocket clasp of the multi-function tool;

FIG. 12A is an enlarged front view of an integrated pill crusher of the multi-function tool;

FIG. 12B is an enlarged right side view of the integrated pill crusher of the multi-function tool;

FIG. 12C is an enlarged left side view of the integrated pill crusher of the multi-function tool;

Corresponding reference numerals indicate corresponding parts throughout the several figures of the drawings.

DETAILED DESCRIPTION

Figure 1:
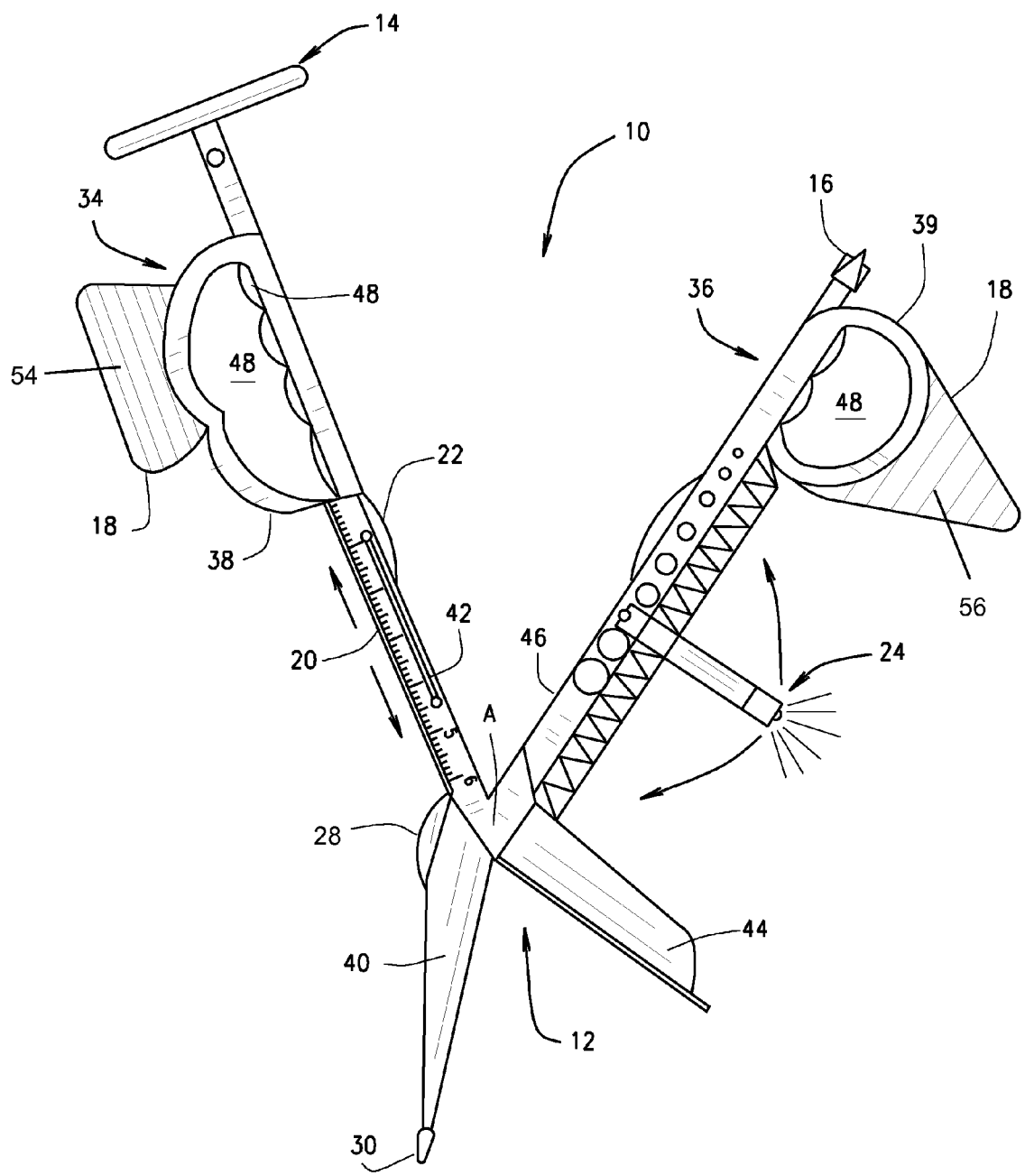
FIG. 1 is a front view of a multi-function tool.
Figure 2:
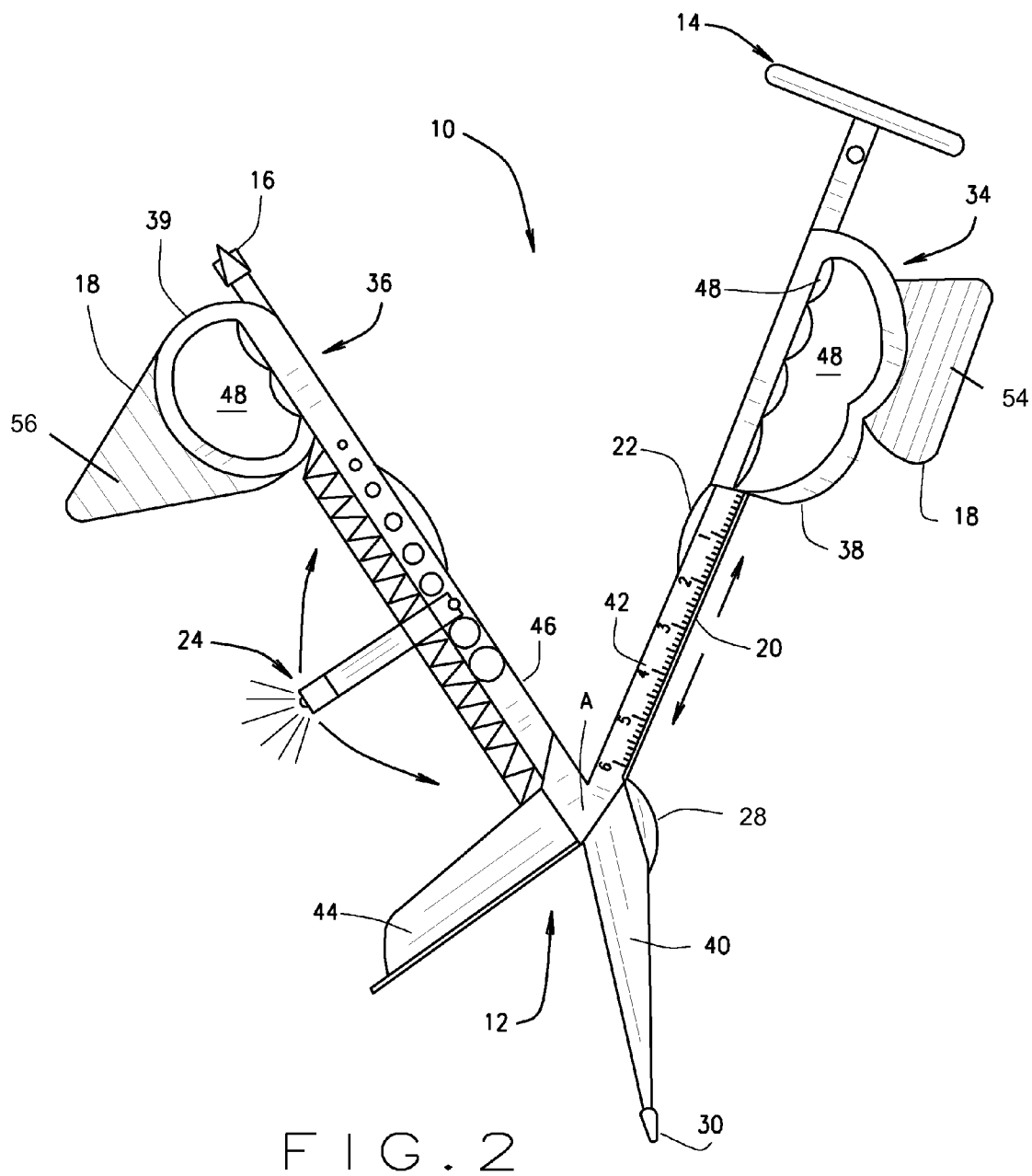
FIG. 2 is a rear view of the multi-function tool.

The following detailed description illustrates the claimed invention by way of example and not by way of limitation. The description clearly enables one skilled in the art to make and use the claimed invention, describes several embodiments, adaptations, variations, alternatives, and uses of the claimed invention, including what is presently believed to be the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

As shown in FIGS. 1-14C, a multi-function tool 10, includes generally a pair of scissors 12 with a plurality of integrated tools including a Babinski reflex hammer 14, screw bit 16, a Taylor reflex hammer 18, a medical slide ruler 20, plier grips 22, a pair of pupil dilator lights 24, a nerve stimulator pin 26, a pill crusher 28, a pill cutter 30, and a nail file 32. These tools are all integrated into a unitary tool 10 that can be carried and used by a medical professional.

In the embodiment of FIGS. 1-14C, the scissors 12 are preferably a pair of bandage scissors having a first arm 34 and a second arm 36 pivotally connected at a pivot point A for moving between an open position and a closed position. However, other types of scissors can also be used. The first arm 34 includes a first handle 38, a first blade 40, and a first shank 42 extending therebetween. The second arm 36 includes a second handle 39, a second blade 44, and a second shank 46 extending therebetween. Each handle 38 and 39 is generally ring-shaped and define openings 48 configured for receiving a user's fingers and thumb. Preferably, the handles 38 and 39 are configured for use by both left-handed and right-handed users. Each handle 38 and 39 can be configured to provide an ergonomic fit. Sizers 48 and attached along an inner portion 50 of each handle 38 and 39 to provide an adjustable fit for multiple users. The sizers 48 are preferably made of an elastic or rubber material that compresses and expands to accommodate the user's fingers. The scissors 12 are preferably made from stainless steel, however, any suitable material can be used, including polymers.

A Taylor reflex hammer 18 attaches to an outer portion of the first handle 38 and the outer portion of the second handle 39. Typically, a Taylor reflex hammer 18 is a generally triangular shaped rubber component used for medical tests, such as test tendon reflexes or chest percussions. In the embodiment of FIGS. 1-14C, the Taylor reflex hammer 18 is divided into a first portion 54 attached to the first handle 38 and a second portion 56 attached to the second handle 39. When the tool 10 is in the closed position, the first portion 54 and second portion 56 are arranged to effectively for a Taylor reflex hammer 18. The user can grasp the tool 10 along the shanks 42 and 46 and blades 40 and 44 for use of the Taylor reflex hammer in the conventional manner. (FIGS. 4A-4D).

A Babinski reflex hammer 14 attaches to the end of the first handle 38. A stem 60 extends from the end of the first handle 38. A generally circular disc 62 having a weighted inner disc 64 surrounded by an outer rubber ring 66 is detachably connected to the stem 60 a multiple points on each side of the stem 60 and the end of the stem 60, such as with threaded posts. The Babinski reflex hammer 14 is used by medical professionals to test tendon reflexes or chest percussions. (FIGS. 3A-3D).

The screw bit 70 is detachably connected to a threaded stem 71 extending from the end of the second handle 39. The screw bit 70 is preferably a Phillips type, but can also be any other suitable screw bit, such as standard, torx, and the like. In addition, the screw bit can be magnetized. (FIGS. 4A-4D).

The first shank 42 includes a medical slide ruler 20. The ruler 20 includes a scale 72, preferably from about 0-6 cm in length, marked along the shank 42. The scale 72 can be marked using any suitable process, such as ink, laser marking, and the like. A slot 74 extends approximately the length of the scale 72. A fastener 76, such as a rivet and washers, moveably resides within the slot 74 for medical measurements such as wound measurements, EKG wave form analysis, and the like. (FIGS. 6A-6B).

Figure 7:
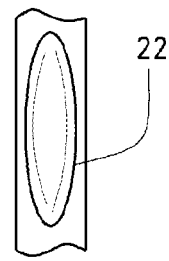
FIG. 7 is an enlarged side view of the integrated plier grips of the multi-function tool.

Plier grips 22 are attached to an inner surface of the first shank 42 and the second shank 46. Preferably the plier grips 80 are rubber pads, about 1 mm thick, that aid gripping an object between the plier grips 80 when the tool 10 is in the closed position. (FIG. 7).

Figure 8:
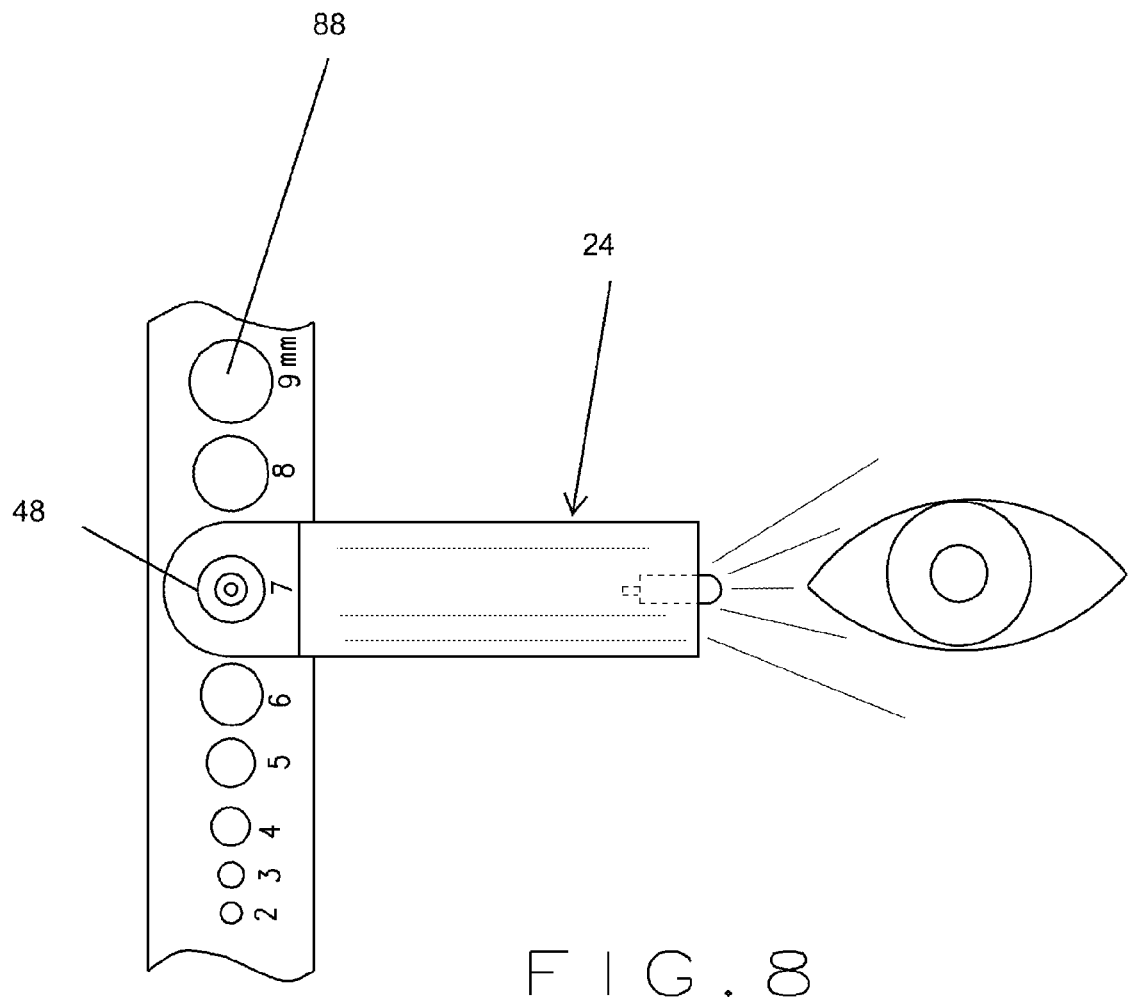
FIG. 8 is an enlarged front view of an integrated pupil dilator of the multi-function tool.
Figure 9A:
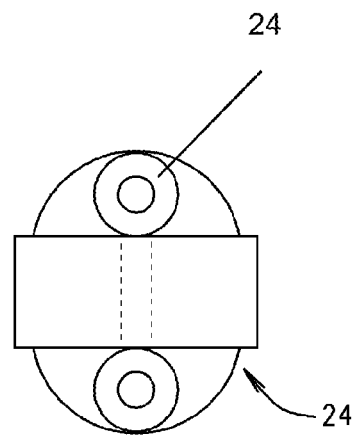
FIG. 9A is an end view of an integrated pair of an pupil dilators of the multi-function tool.
Figure 9B:
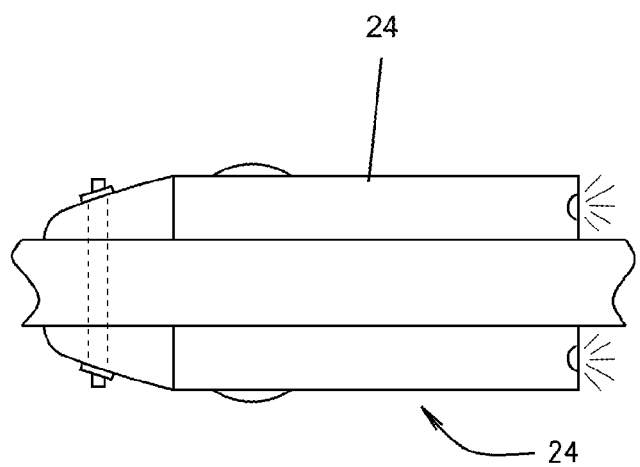
FIG. 9B is a side view of the integrated pair of pupil dilators of the multi-function tool.
Figure 10A:
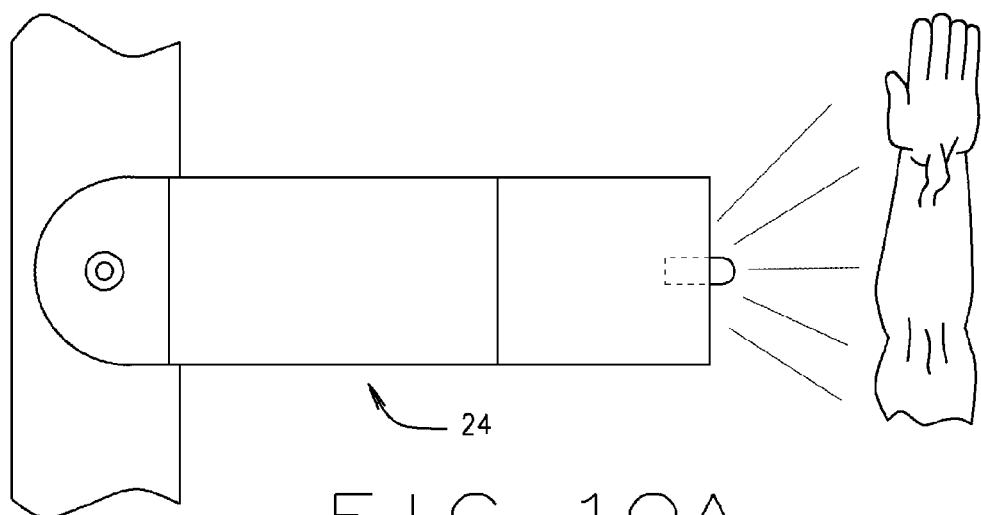
FIG. 10A is a front view of a vein sleeve engaged with the pupil dilator of the multi-function tool.
Figure 10B:
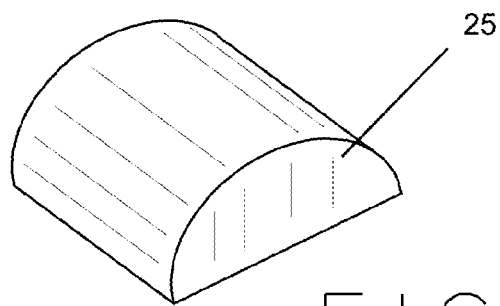
FIG. 10B is a perspective view of the vein sleeve.
Figure 12D:
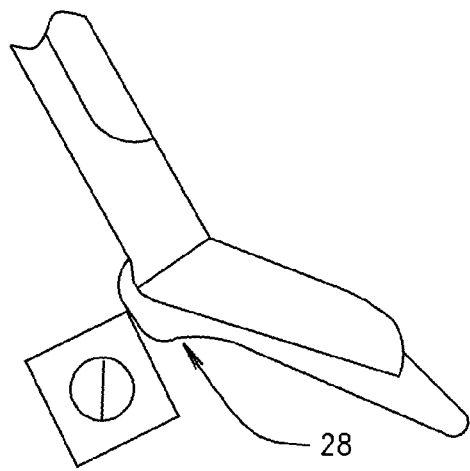
FIG. 12D is an enlarged front view of the integrated pill crusher of the multi-function tool crushing a pill.

A pair of pupil dilator lights 24 are pivotally attached to each side of the second shank 46, such as with a rivet 48. (FIGS. 8-9B). Each light 24 includes a generally half-cylinder shaped housing 84 that encloses a power source, such as a battery, and a switch 86. Each light 24 can pivot between a storage position, where the light is generally parallel with the second shank 46, and an operating position, where the light is generally perpendicular with the second shank 46. In the storage position, the lights 24 can provide light to aid use of the scissors. In the operating position, the lights 24 can provide light for a pupil dilator test. The lights 24 are preferably bright enough to perform a pupil dilator test, such as about 1000 lumens. Indicia 88 along the second shank 46 depict a pupil diameter scale from about 2 mm to about 9 mm. In an alternate embodiment, a ultraviolet fluorescent sleeve 25 fits over one or both of the lights 24. Under darkened room conditions, The light emitted through the sleeve aids detection of veins to about 5 mm deep. (FIGS. 10A-10B)

The first shank 42 includes a pocket clasp 90 for attaching to a user's pocket. The clasp defines a bore 92 sized to receive a nerve stimulator pin 26. (FIG. 11B).

Figure 13A:
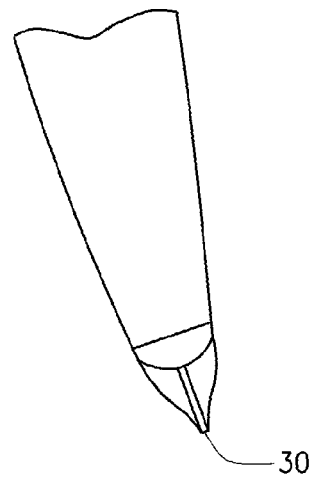
FIG. 13A is an enlarged front view of an integrated pill splitter of the multi-function tool.
Figure 13B:
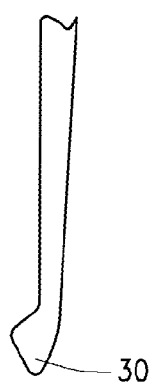
FIG. 13B is an enlarged right side view of the integrated pill splitter of the multi-function tool.
Figure 13C:
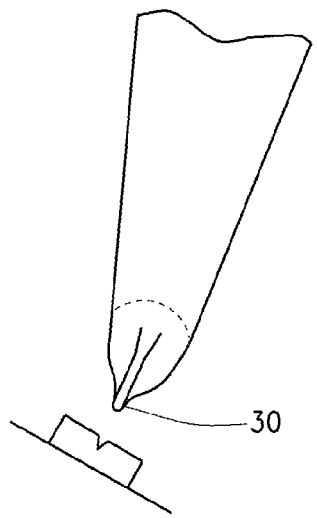
FIG. 13C is an enlarged front view of the integrated pill splitter of the multi-function tool splitting a pill.

The outer portion of the second blade 44 includes a pill crusher 28. The pill crusher 96 is a generally curved surface, which a user presses onto a pill to crush into a powder or smaller pieces. Preferably, the pill remains sealed within a protective package during the crushing process. (FIGS. 12A-12D). The tip of the second blade 44 includes a pill splitter 30, which is generally a linear edge about the length of a typical pill. In use, the user presses the edge onto a pill until it splits into two halves. (FIGS. 13A-13C).

Figure 14A:
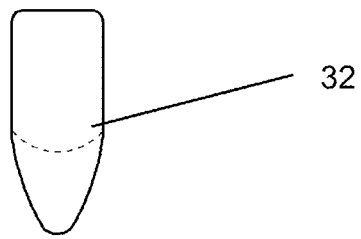
FIG. 14A is an enlarged end view of an integrated file of the multi-function tool.
Figure 14B:
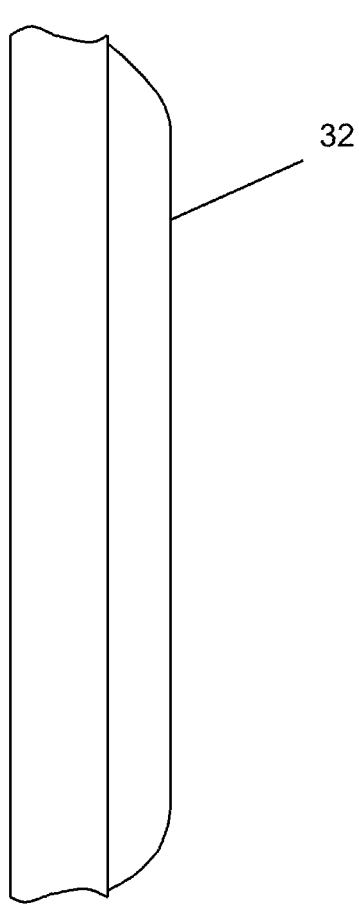
FIG. 14B is an enlarged front view of the integrated file of the multi-function tool.
Figure 14C:
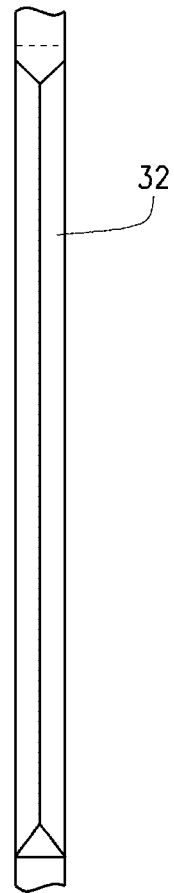
FIG. 14C is an enlarged side view of the integrated file of the multi-function tool.
Figure 15:
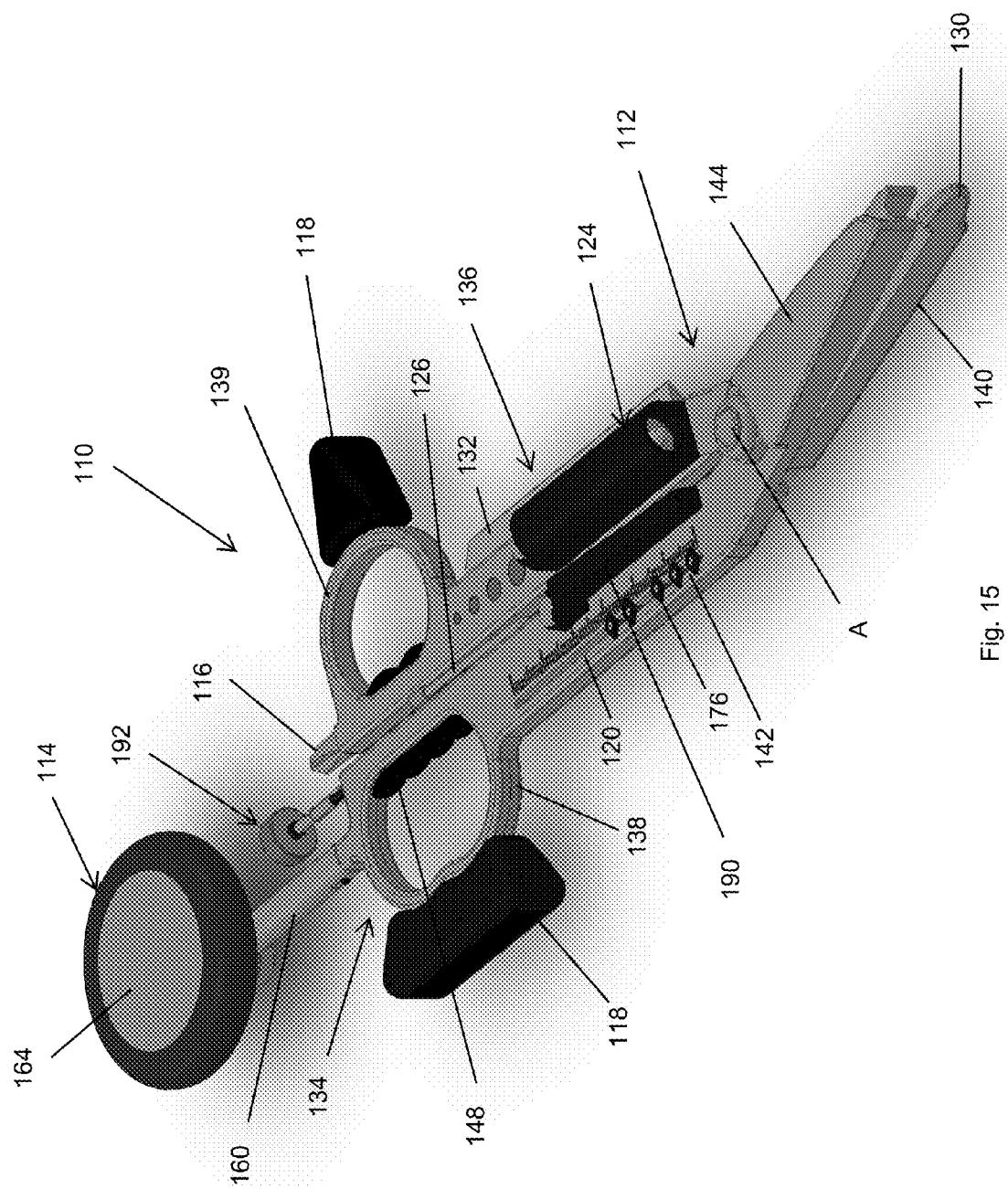
FIG. 15 is a perspective view of an alternate embodiment of a multi-function tool.

The interior surface of either shank 42 and 46 can include a nail file 32. (FIGS. 14A-14C).

All or a portion of tool 10 can be coated with a suitable material, such as a polymer, to enhance ease of cleaning and disinfection.

As shown in FIGS. 15-22, an alternate embodiment of a multi-function tool 110, includes generally a pair of scissors 112 with a plurality of integrated tools including a Babinski reflex hammer 114, screw bit 116, a Taylor reflex hammer 118, a medical slide ruler 120, plier grips 122, a pair of pupil dilator lights 124, a nerve stimulator pin 126, a pill crusher 128, a pill cutter 130, a nail file 132, and a roller brush 192. These tools are all integrated into a unitary tool 110 that can be carried and used by a medical professional.

In the embodiment of FIGS. 15-22, the scissors 112 are preferably a pair of bandage scissors having a first arm 134 and a second arm 136 pivotally connected at a pivot point A for moving between an open position and a closed position. However, other types of scissors can also be used. The first arm 134 includes a first handle 138, a first blade 140, and a first shank 142 extending therebetween. The second arm 136 includes a second handle 139, a second blade 144, and a second shank 146 extending therebetween. Each handle 138 and 139 is generally ring-shaped and define openings 148 configured for receiving a user's fingers and thumb. Preferably, the handles 138 and 139 are configured for use by both left-handed and right-handed users. Each handle 138 and 139 can be configured to provide an ergonomic fit. Sizers 148 and attached along an inner portion 150 of each handle 138 and 139 to provide an adjustable fit for multiple users. The sizers 148 are preferably made of an elastic or rubber material that compresses and expands to accommodate the user's fingers. The scissors 112 are preferably made from stainless steel, however, any suitable material can be used, including polymers.

A Taylor reflex hammer 118 attaches to an outer portion of the first handle 38 and the outer portion of the second handle 139. Typically, a Taylor reflex hammer 118 is a generally triangular shaped rubber component used for medical tests, such as test tendon reflexes or chest percussions. In the embodiment of FIGS. 15-22, the Taylor reflex hammer 118 is divided into a first portion 154 attached to the first handle 138 and a second portion 156 attached to the second handle 139. When the tool 110 is in the closed position, the first portion 154 and second portion 156 are arranged to effectively for a Taylor reflex hammer 118. The user can grasp the tool 110 along the shanks 142 and 146 and blades 140 and 144 for use of the Taylor reflex hammer in the conventional manner. (FIGS. 4A-4D).

A Babinski reflex hammer 114 attaches to the end of the first handle 138. A stem 160 extends from the end of the first handle 138. A generally circular disc 162 having a weighted inner disc 164 surrounded by an outer rubber ring 166 is detachably connected to the stem 160 a multiple points on each side of the stem 160 and the end of the stem 160, such as with threaded posts. The Babinski reflex hammer 114 is used by medical professionals to test tendon reflexes or chest percussions.

The screw bit 116 is detachably connected to a threaded stem 171 extending from the end of the second handle 139. The screw bit 116 is preferably a Phillips type, but can also be any other suitable screw bit, such as standard, torx, and the like. In addition, the screw bit can be magnetized.

Figure 16:
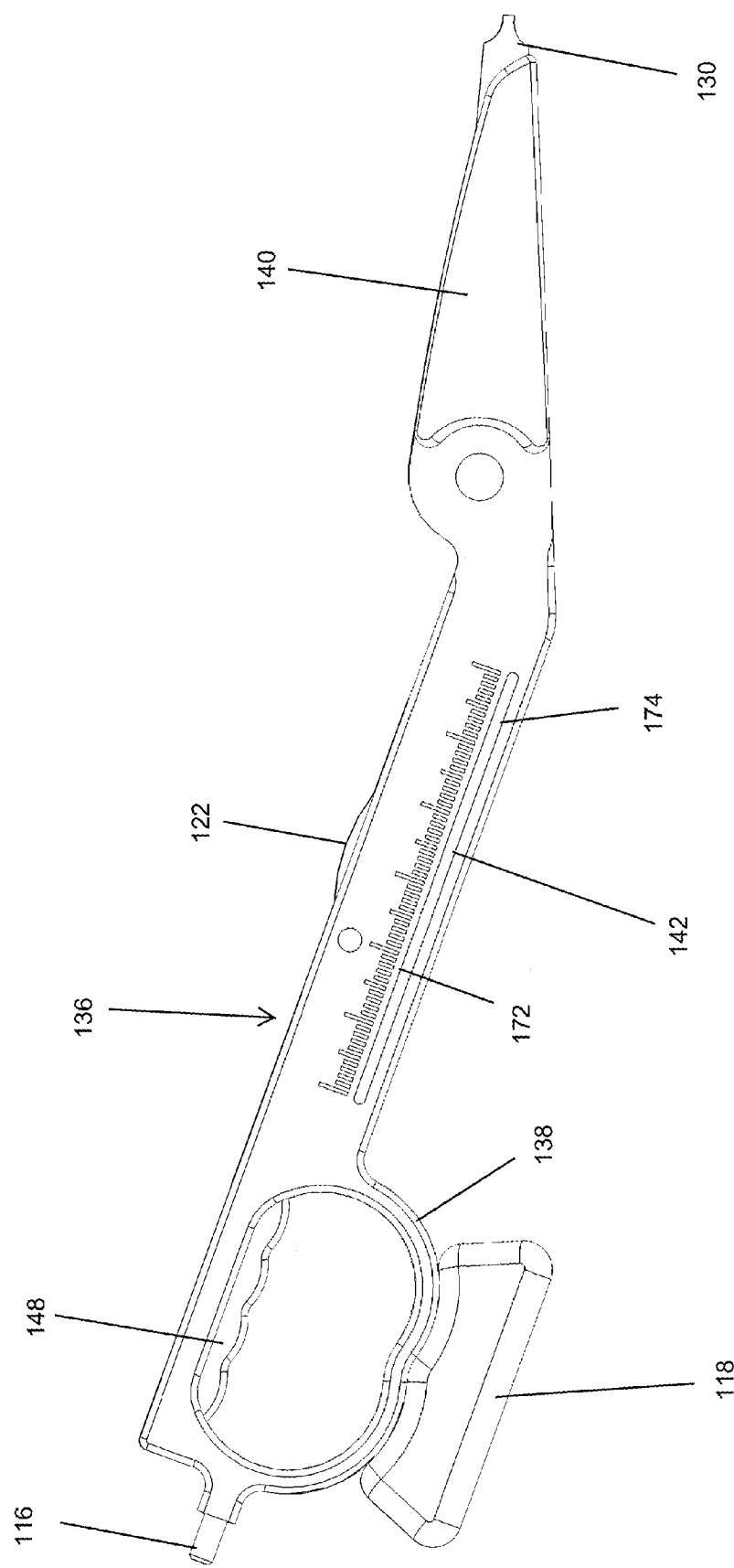
FIG. 16 is a side view of an alternate embodiment of a first arm of the multi-function tool.
Figure 17:
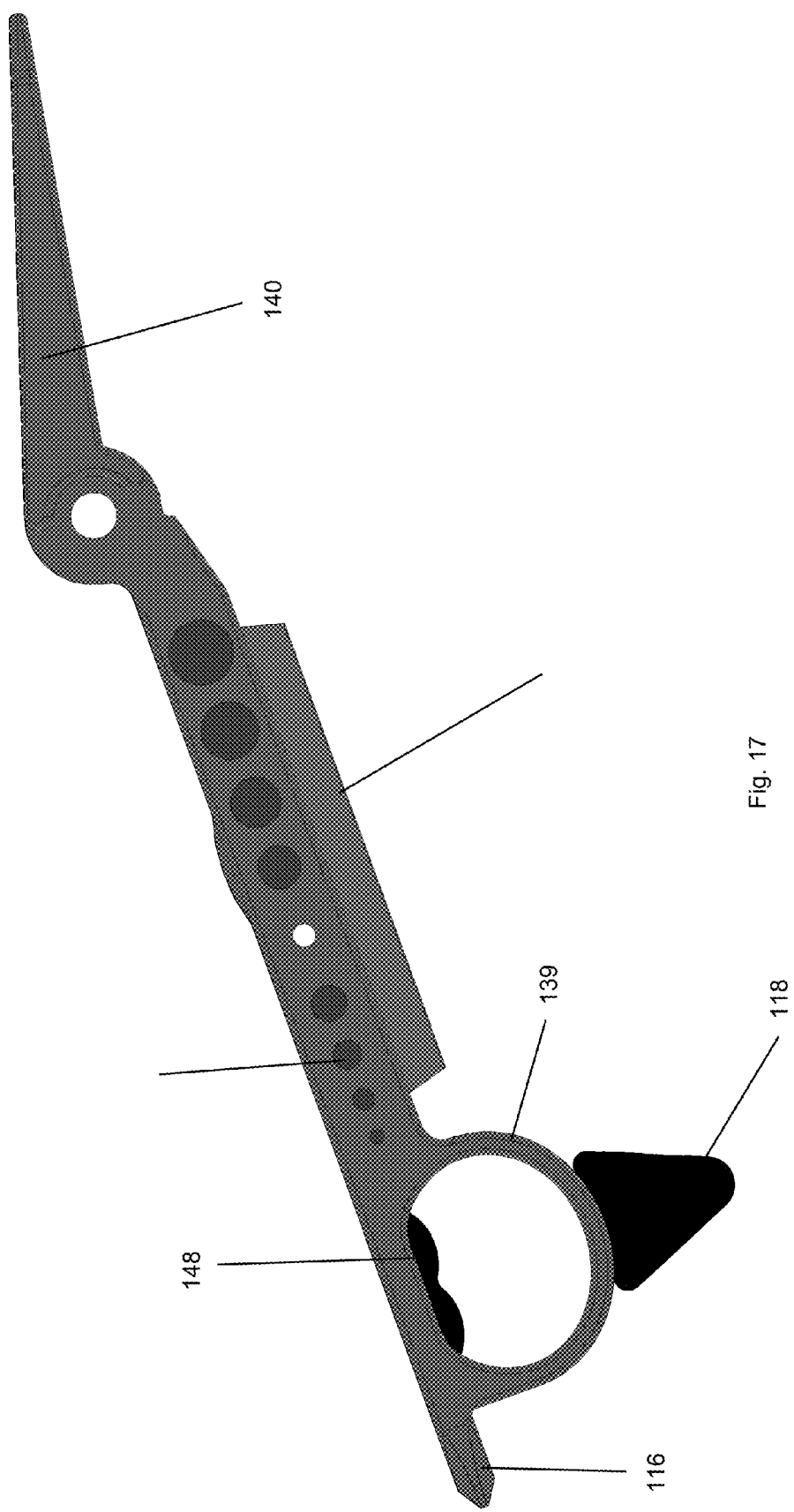
FIG. 17 is a side view of an alternate embodiment of a second arm of the multi-function tool.
Figure 18:
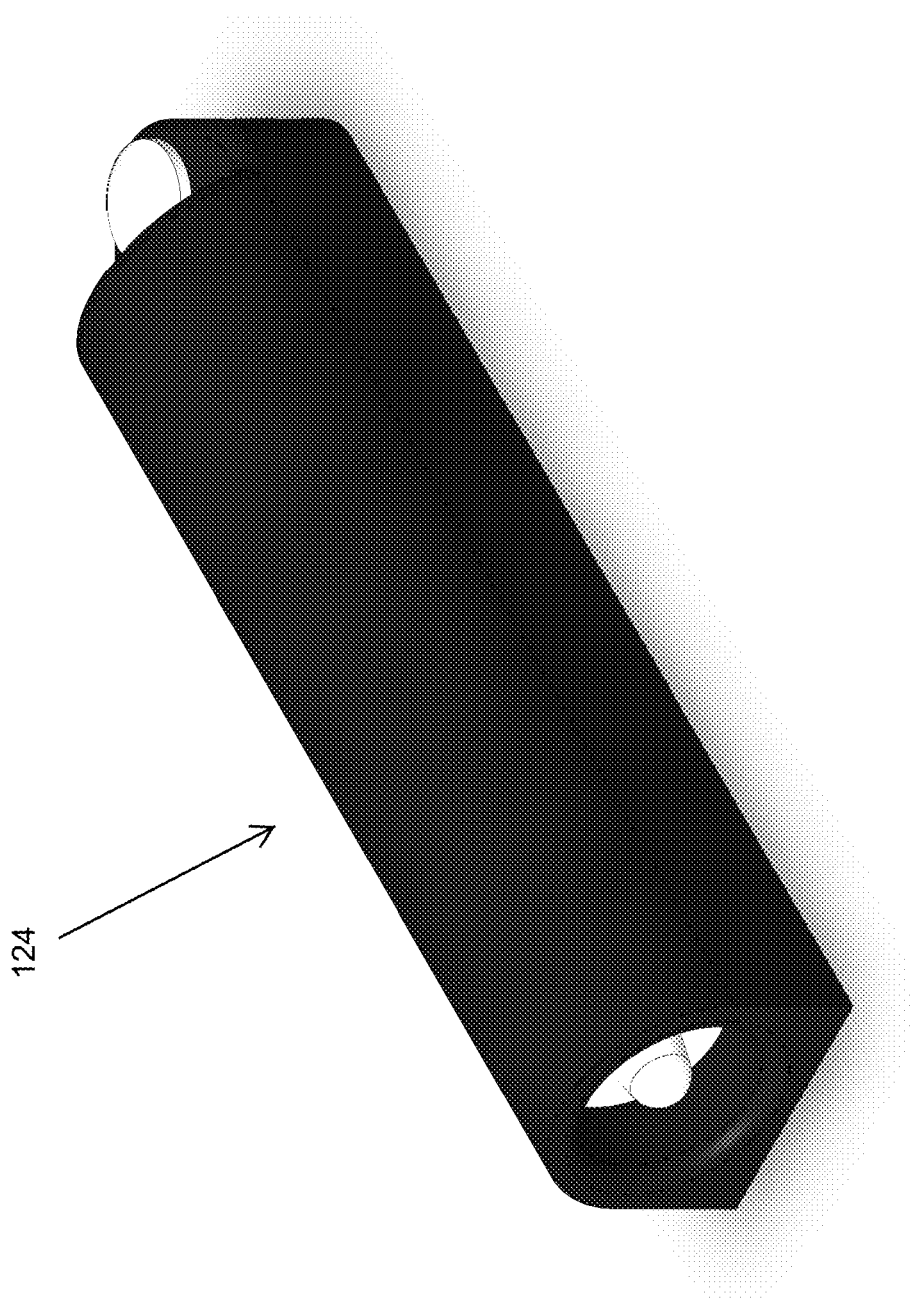
FIG. 18 is a perspective view of an alternate embodiment of a flashlight of the multi-function tool.

The first shank 142 includes a medical slide ruler 120. The ruler 120 includes a scale 172, preferably from about 0-6 cm in length, marked along the shank 42. The scale 172 can be marked using any suitable process, such as ink, laser marking, and the like. A slot 174 extends approximately the length of the scale 172. A fastener 176, such as a rivet and washers, moveably resides within the slot 174 for medical measurements such as wound measurements, EKG wave form analysis, and the like. (FIG. 16).

Plier grips 22 are attached to an inner surface of the first shank 42 and the second shank 46. Preferably the plier grips 80 are rubber pads, about 1 mm thick, that aid gripping an object between the plier grips 80 when the tool 10 is in the closed position. (FIG. 7).

A pair of pupil dilator lights 124 are pivotally attached to each side of the second shank 146, such as with a rivet 148. (FIGS. 8-9B)). Each light 24 includes a generally half-cylinder shaped housing 184 that encloses a power source, such as a battery, and a switch 186. Each light 24 can pivot between a storage position, where the light is generally parallel with the second shank 146, and an operating position, where the light is generally perpendicular with the second shank 146. In the storage position, the lights 124 can provide light to aid use of the scissors. In the operating position, the lights 124 can provide light for a pupil dilator test. The lights 124 are preferably bright enough to perform a pupil dilator test, such as about 1000 lumens. Indicia 188 along the second shank 146 depict a pupil diameter scale from about 2 mm to about 9 mm. In an alternate embodiment, a ultraviolet fluorescent sleeve 125 fits over one or both of the lights 124. Under darkened room conditions, the light emitted through the sleeve aids detection of veins to about 5 mm deep. (FIGS. 10A-10B)

Figure 19:
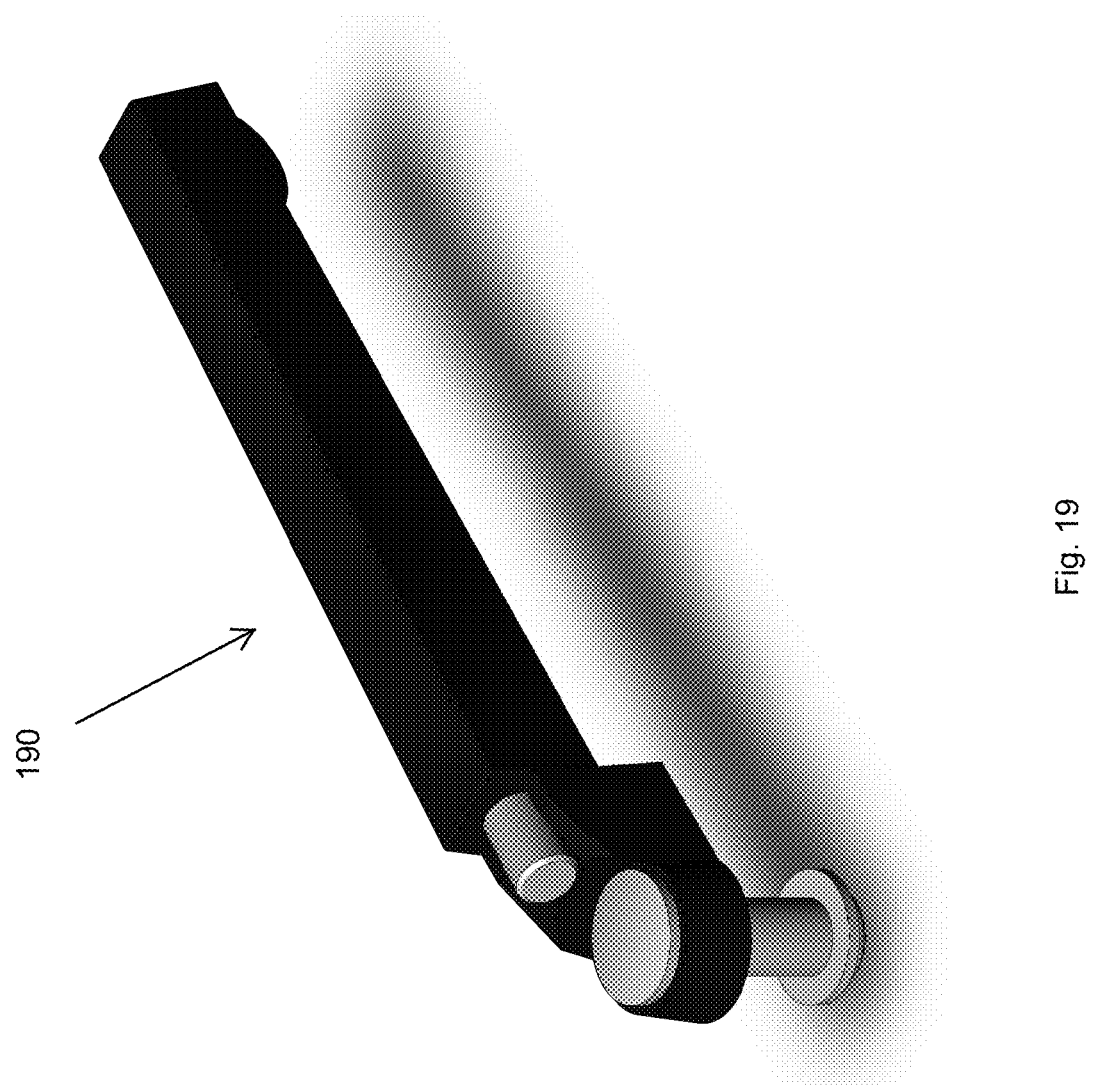
FIG. 19 is a perspective view of an alternate embodiment of an integrated pocket clasp of the multi-function tool.
Figure 20:
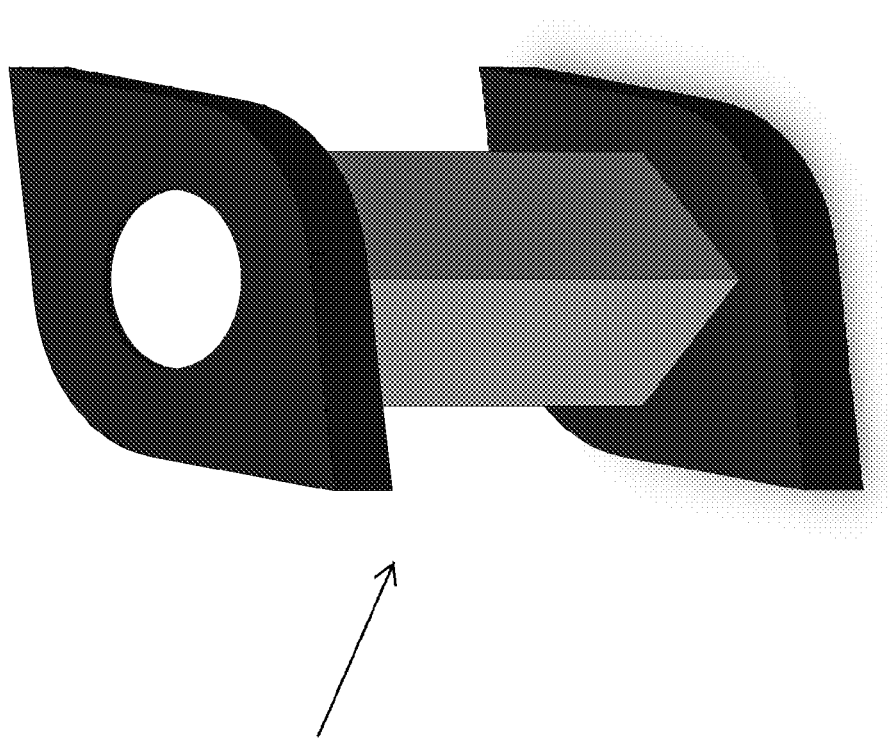
FIG. 20 is a perspective view of a pointer of the multi-function tool.
Figure 21:
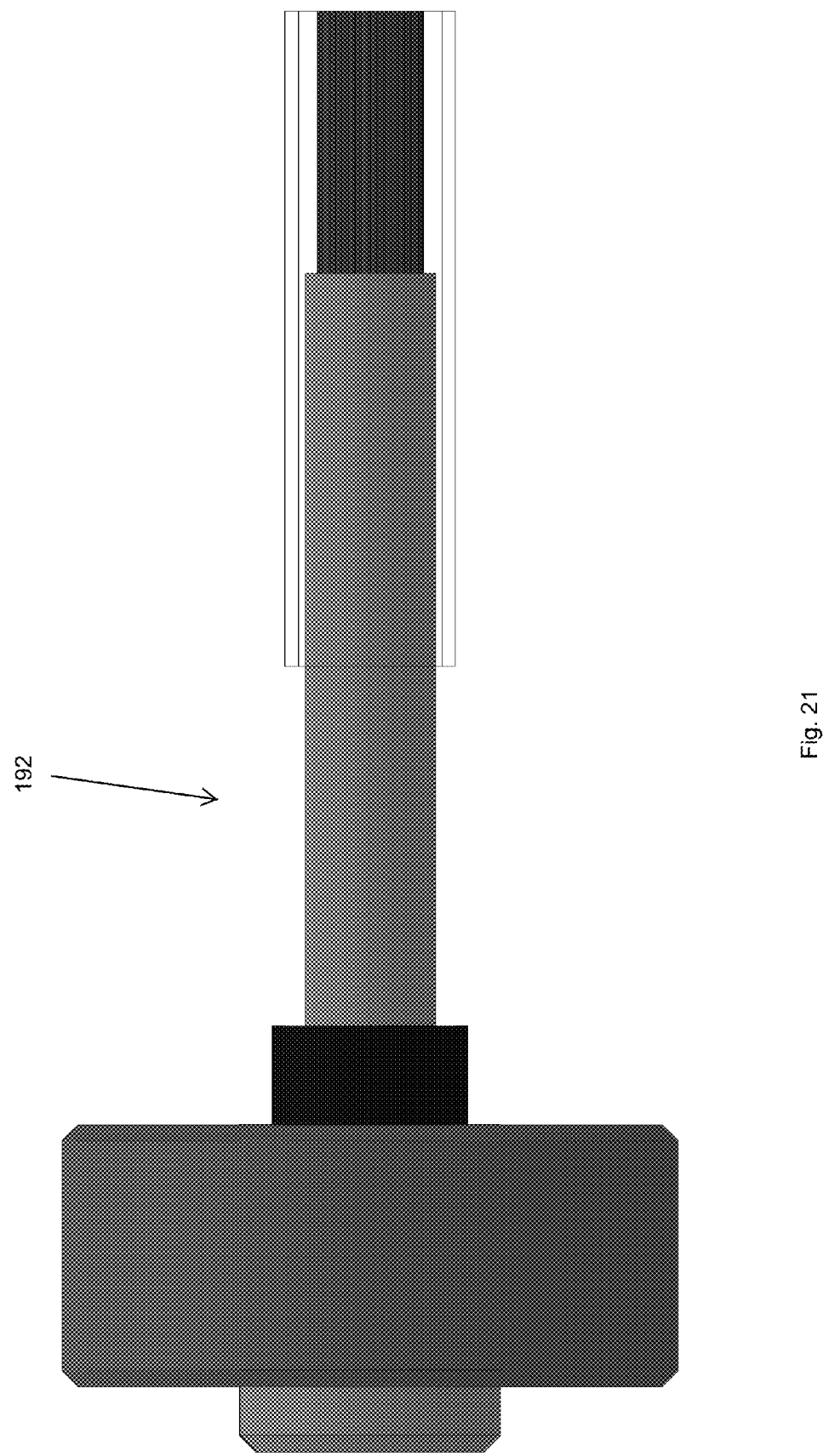
FIG. 21 is a side view of a roller brush of the multi-function tool.
Figure 22:
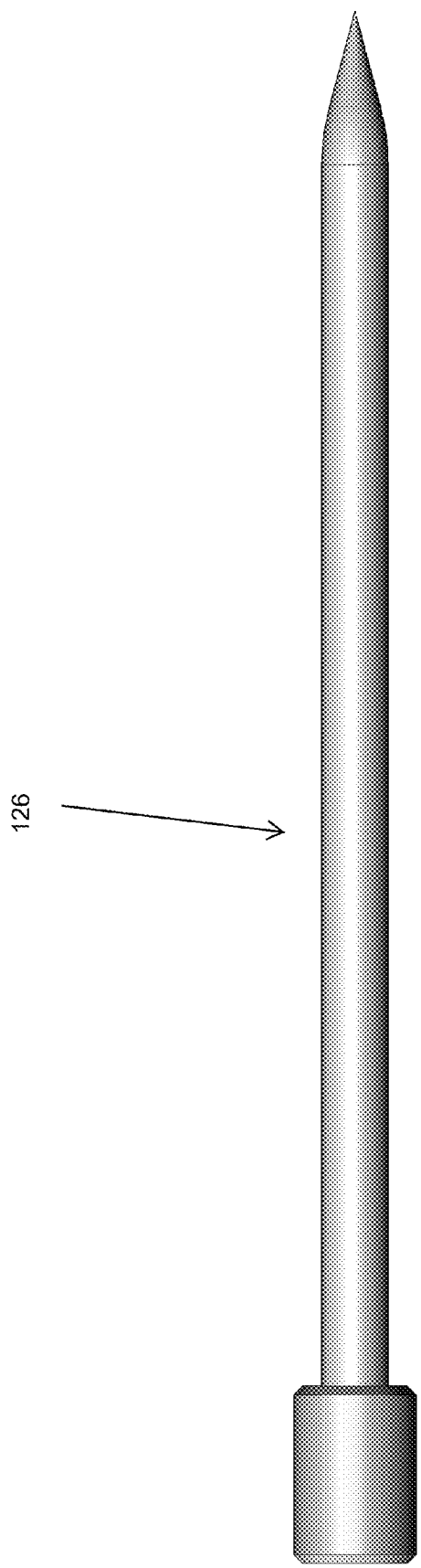
FIG. 22 is a side view of a nerve stimulator pin of the multi-function tool.

The first shank 142 includes a pocket clasp 190 for attaching to a user's pocket. The clasp defines a bore 192 sized to receive a nerve stimulator pin 126. (FIG. 19).

The outer portion of the second blade 144 includes a pill crusher 128. The pill crusher 196 is a generally curved surface, which a user presses onto a pill to crush into a powder or smaller pieces. Preferably, the pill remains sealed within a protective package during the crushing process. (FIGS. 12A-12D). The tip of the second blade 144 includes a pill splitter 130, which is generally a linear edge about the length of a typical pill. In use, the user presses the edge onto a pill until it splits into two halves. (FIGS. 13A-13C).

The interior surface of either shank 142 and 146 can include a nail file 132. (FIGS. 14A-14C).

All or a portion of tool 110 can be coated with a suitable material, such as a polymer, to enhance ease of cleaning and disinfection.

Changes can be made in the above constructions without departing from the scope of the invention, it is intended that all matter contained in the above description or shown in the accompanying drawings shall be interpreted as illustrative and not in a limiting sense.

What is claimed is:

1. A multifunction health professional tool, comprising:
a pair of scissors having a pair of blades and a pair of handles connected by a pair of shanks;
a Babinski reflex hammer detachably connected to one of the handles;
a Taylor reflex hammer, divided into a first and second portion, wherein the first portion is connected to one of the handles and a second portion is connected to the opposing handle;
a slide ruler attached to one of the shanks;
a pupil dilator light attached to one of the shanks; and
an ultraviolet fluorescent sleeve configured for attachment to the pupil attachment light for enhancement of detection of a patients veins.

2. The multifunction health professional tool of claim 1, further comprising a nerve stimulator pin.

3. The multifunction health professional tool of claim 1, further comprising pill splitter attached to an end of one of the blades.

4. The multifunction health professional tool of claim 1, further comprising pill crusher attached to an outer portion of one of the blades.

5. The multifunction health professional tool of claim 1, further comprising pocket clasp.

6. The multifunction health professional tool of claim 1, further comprising a rollerbrush attached to one of the handles.

7. The multifunction health professional tool of claim 1, further comprising a file attached to one of the shanks.

8. The multifunction health professional tool of claim 1, further comprising a flashlight attached to one of the shanks.

9. The multifunction health professional tool of claim 1, further comprising a screw bit detachably connected to an end of one of the handles.

10. The multifunction health professional tool of claim 1, further comprising a pair of plier grips attached to respective inner surfaces of the pair of shanks.

11. A multifunction health professional tool, comprising:
a pair of scissors having a pair of blades and a pair of handles connected by a pair of shanks;
a Taylor reflex hammer, divided into a first and second portion, wherein the first portion is connected to one of the handles and a second portion is connected to the opposing handle;

a slide ruler attached to one of the shanks;
a pill crusher attached to an outer portion of one of the blades; and
an ultraviolet fluorescent sleeve configured for attachment to the pupil attachment light for enhancement of detection of a patients veins.

12. A multifunction health professional tool, comprising:
a pair of scissors having a pair of blades and a pair of handles connected by a pair of shanks;
a Babinski reflex hammer detachably connected to one of the handles;
a slide ruler attached to one of the shanks;
a pupil dilator light attached to one of the shanks; and
an ultraviolet fluorescent sleeve configured for attachment to the pupil attachment light for enhancement of detection of a patients veins.

13. The multifunction health professional tool of claim 12, further comprising a nerve stimulator pin.

14. The multifunction health professional tool of claim 12, further comprising pill splitter attached to an end of one of the blades.

15. The multifunction health professional tool of claim 12, further comprising pill crusher attached to an outer portion of one of the blades.

16. The multifunction health professional tool of claim 12, further comprising pocket clasp.

* * * * *